(12) United States Patent
Houde et al.

(10) Patent No.: US 10,543,054 B2
(45) Date of Patent: Jan. 28, 2020

(54) STERILIZATION PACKAGING SYSTEMS

(71) Applicant: O&M Halyard, Inc., Mechanicsville, VA (US)

(72) Inventors: Ajay Y. Houde, Johns Creek, GA (US); Joseph D. Hurdle, Canton, GA (US); Joseph A. Cesa, Cumming, GA (US); Michelle N. Farmer, Marietta, GA (US); Prasad Shrikishna Potnis, Johns Creek, GA (US)

(73) Assignee: O&M Halyard, Inc., Mechanicsville, VA (US)

( * ) Notice: Subject to any disclaimer, the term of this patent is extended or adjusted under 35 U.S.C. 154(b) by 0 days.

(21) Appl. No.: 15/522,465

(22) PCT Filed: Oct. 26, 2016

(86) PCT No.: PCT/US2016/058778
§ 371 (c)(1),
(2) Date: Apr. 27, 2017

(87) PCT Pub. No.: WO2017/075000
PCT Pub. Date: May 4, 2017

(65) Prior Publication Data
US 2018/0221525 A1 Aug. 9, 2018

Related U.S. Application Data

(60) Provisional application No. 62/248,401, filed on Oct. 30, 2015.

(51) Int. Cl.
*A61B 50/33* (2016.01)
*A61L 2/26* (2006.01)
(Continued)

(52) U.S. Cl.
CPC .............. *A61B 50/33* (2016.02); *A61L 2/07* (2013.01); *A61L 2/14* (2013.01); *A61L 2/206* (2013.01);
(Continued)

(58) Field of Classification Search
CPC ..... A61L 2/26; F16K 35/10; A61B 2050/007; A61B 2050/0074; B65D 45/32
(Continued)

(56) References Cited

U.S. PATENT DOCUMENTS 1,782,120 A    11/1930  Funke
1,994,214 A     3/1935  Frost
(Continued)

FOREIGN PATENT DOCUMENTS

DE    42 38 535 A1    5/1994
JP    S 4625682 Y1   7/1971
(Continued)

OTHER PUBLICATIONS

International Search Report and Written Opinion, dated Feb. 17, 2017, 10 pages.

*Primary Examiner* — Andrew T Kirsch
(74) *Attorney, Agent, or Firm* — Dority & Manning, P.A.

(57) ABSTRACT

Sterilization packaging systems with features for sealing a volume against an ingress of contaminants are provided. Such features include a sealing assembly, where the sealing assembly includes a sheet of sterilization material and a clamp for sealing the sheet of sterilization material against a container to seal the volume of the container from contaminants. Also provided is a sealing assembly including a sheet of sterilization material and a clamp having open position and clamped positions. The clamp is configured to extend about a perimeter of a container, the sheet of sterilization material is disposed between the container and the
(Continued)

clamp when the clamp is in the clamped position to seal a volume of the container, and the clamp is held in the clamped position by a latch. Exemplary sterilization packaging systems may include other features as well.

20 Claims, 11 Drawing Sheets

(51) Int. Cl.
| | | |
|---|---|---|
| *B65D 45/32* | (2006.01) | |
| *A61L 2/20* | (2006.01) | |
| *A61L 2/07* | (2006.01) | |
| *A61L 2/14* | (2006.01) | |
| *B65D 21/02* | (2006.01) | |

(52) U.S. Cl.
CPC .............. *A61L 2/208* (2013.01); *A61L 2/26* (2013.01); *B65D 21/0219* (2013.01); *B65D 45/32* (2013.01); *A61L 2202/24* (2013.01)

(58) Field of Classification Search
USPC ............................................................ 220/321
See application file for complete search history.

(56) References Cited

U.S. PATENT DOCUMENTS

| | | | |
|---|---|---|---|
| 2,121,307 A | 6/1938 | Swift | |
| 2,816,559 A * | 12/1957 | Kuhar, Jr. ............... | E04H 15/04 135/120.3 |
| 3,105,787 A * | 10/1963 | Carpenter, Sr. ....... | B31F 1/0009 156/222 |
| 3,730,338 A | 5/1973 | Chesky | |
| 3,866,794 A * | 2/1975 | Kerr ...................... | B65D 45/32 220/256.1 |
| 4,041,203 A | 8/1977 | Brock et al. | |
| 4,135,657 A * | 1/1979 | Benson ................ | B65D 45/345 220/321 |
| 4,206,844 A * | 6/1980 | Thukamoto ........... | A61F 15/001 206/439 |
| 4,305,535 A * | 12/1981 | Brundige ............ | B65D 21/0222 220/780 |
| 4,387,922 A * | 6/1983 | Geisinger .............. | B65D 25/32 215/396 |
| 4,466,552 A | 8/1984 | Butterworth et al. | |
| 4,661,326 A | 4/1987 | Schainholz | |
| 4,671,943 A | 6/1987 | Wahlquist | |
| 4,706,839 A | 11/1987 | Spence | |
| 4,774,063 A | 9/1988 | Runnells | |
| 4,798,292 A | 1/1989 | Hauze | |
| 4,932,554 A * | 6/1990 | Smith .................. | B65D 43/022 220/285 |
| 5,098,676 A | 3/1992 | Brooks, Jr. | |
| 5,439,132 A * | 8/1995 | Gorlich .................. | B65B 7/168 200/258 |
| 5,947,320 A * | 9/1999 | Bordner ............. | B65D 43/0218 220/321 |
| 6,276,552 B1 * | 8/2001 | Vervisch ................ | F16K 35/10 220/315 |
| 6,629,602 B1 | 10/2003 | Heyman | |
| 7,243,962 B2 * | 7/2007 | Stolzman ............. | B65D 45/345 292/256.65 |
| 7,942,264 B2 | 5/2011 | Friderich et al. | |
| 8,241,587 B2 | 8/2012 | Friderich et al. | |
| 8,418,872 B2 | 4/2013 | Smith | |
| 8,733,551 B2 | 5/2014 | Parker et al. | |
| 9,028,146 B2 | 5/2015 | Brimson | |
| 2003/0183540 A1 | 10/2003 | Onishi | |
| 2010/0154353 A1 | 6/2010 | Cesa et al. | |
| 2011/0127188 A1 | 6/2011 | Thompson et al. | |
| 2011/0139650 A1* | 6/2011 | Dworak .................... | A61L 2/26 206/363 |
| 2012/0152289 A1 | 6/2012 | Smith et al. | |

FOREIGN PATENT DOCUMENTS

| | | |
|---|---|---|
| JP | H 10113142 A | 5/1998 |
| JP | 3184488 U | 6/2013 |
| WO | WO 2010/042847 A1 | 4/2010 |
| WO | WO 2010061876 A1 | 6/2010 |

\* cited by examiner

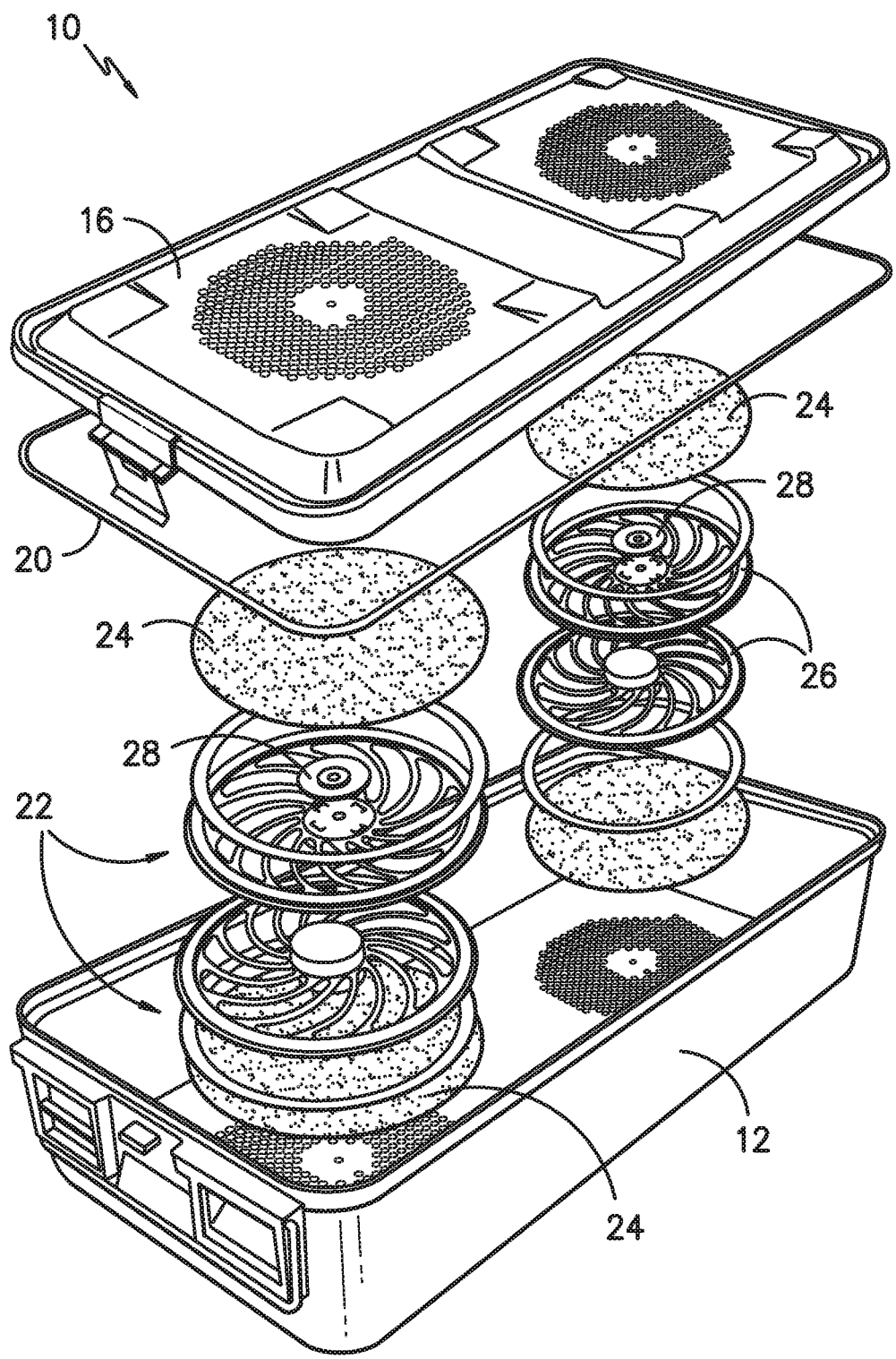
FIG. -1-
PRIOR ART

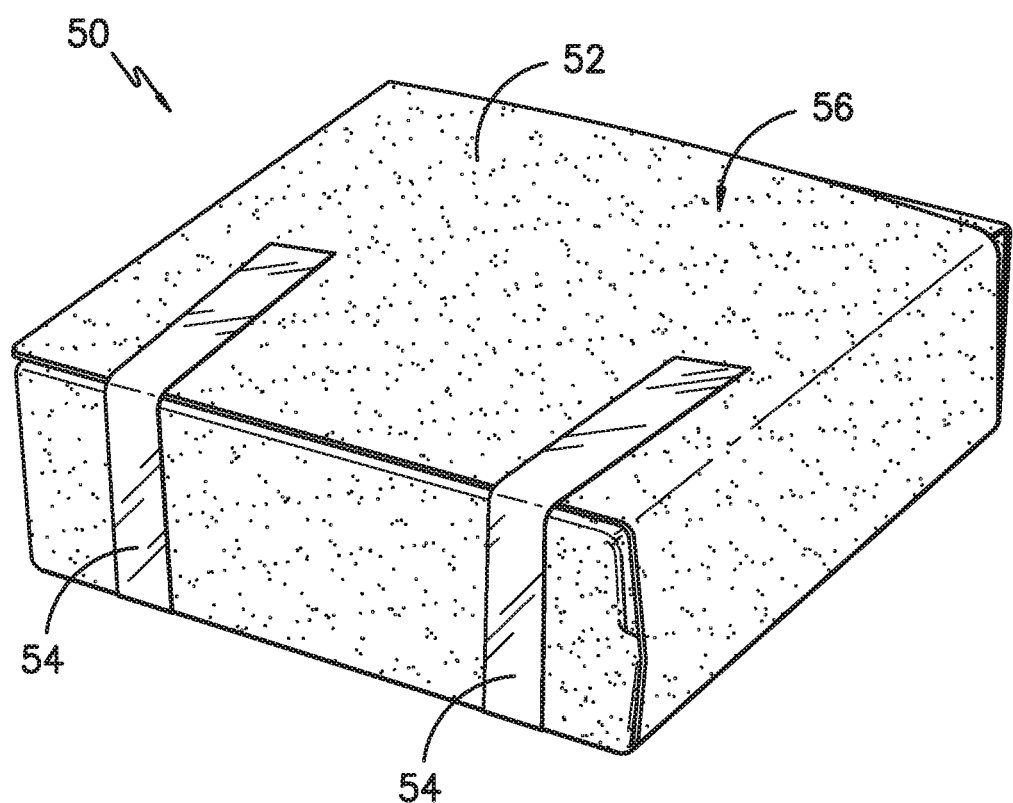
FIG. -2-
PRIOR ART

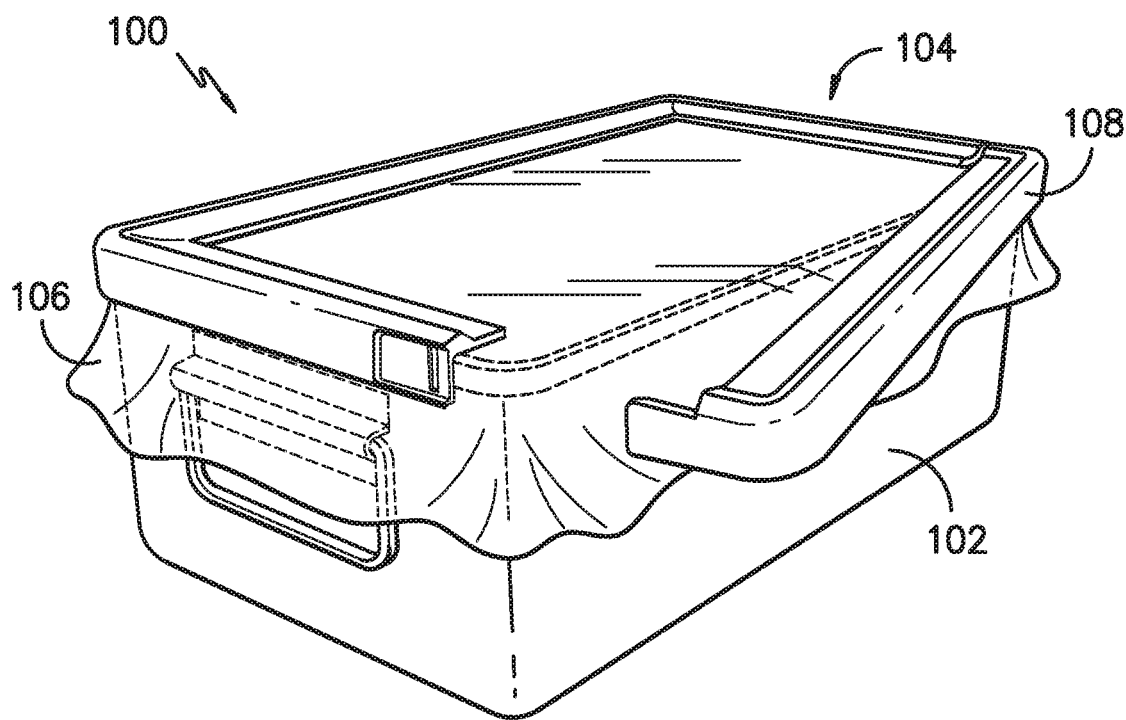
FIG. -3-
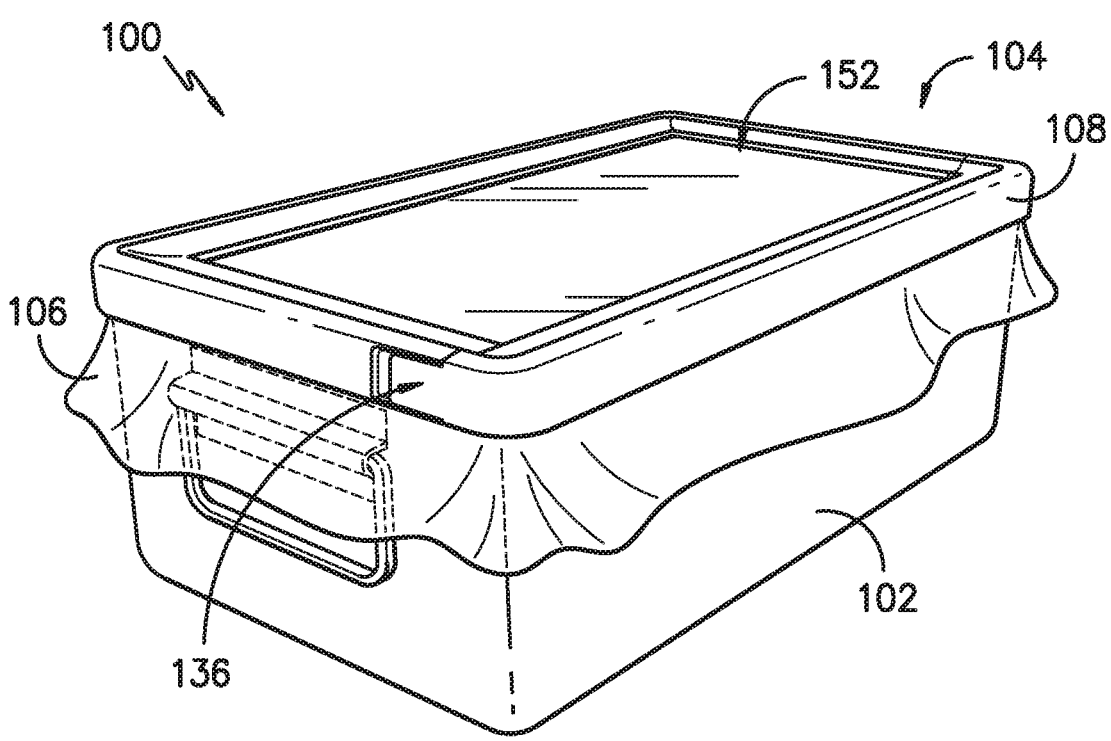
FIG. -4-

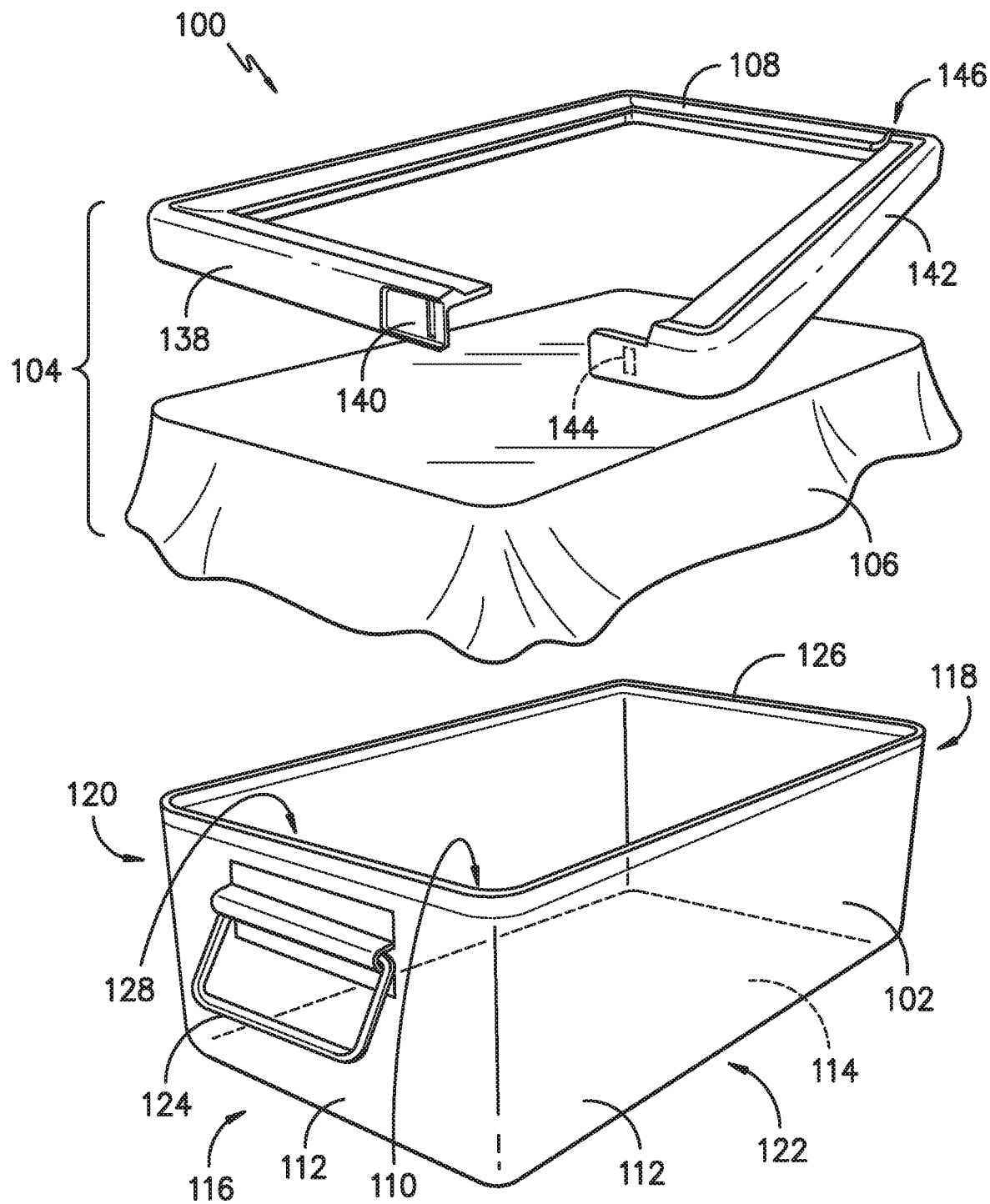
FIG. -5-

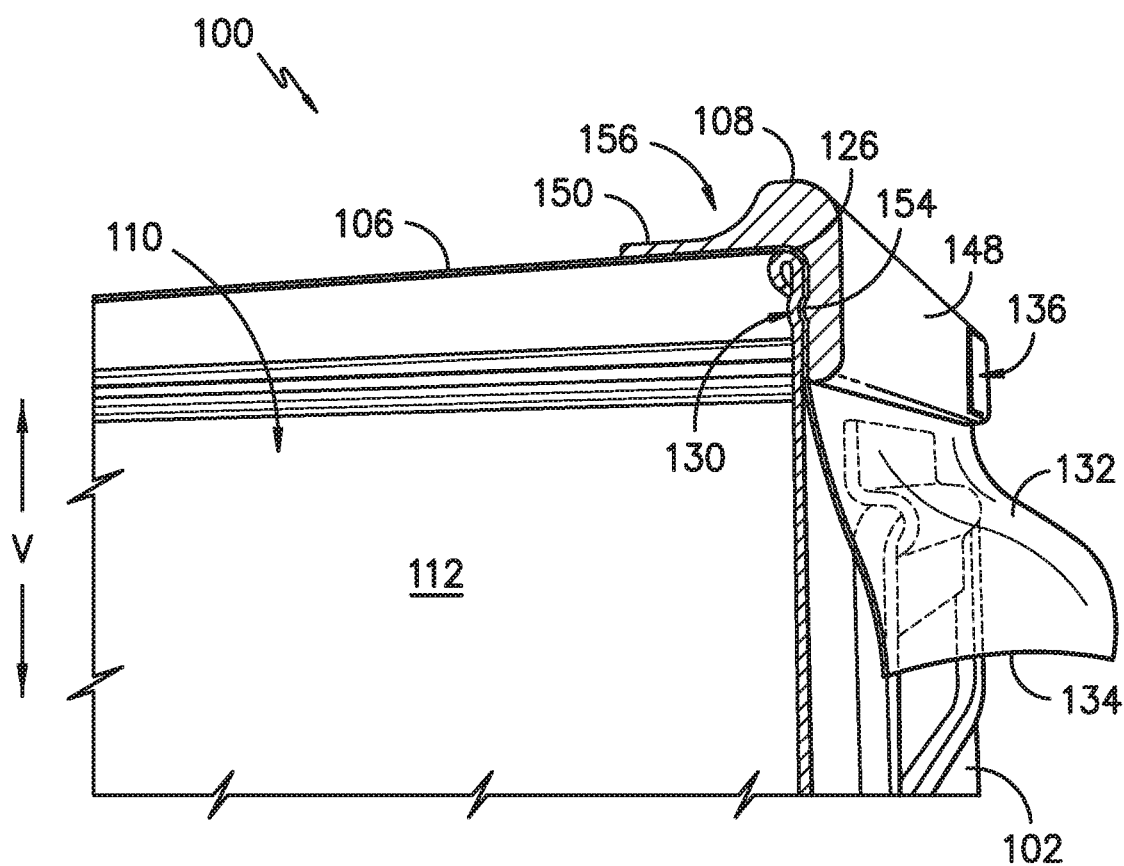
FIG. -6-

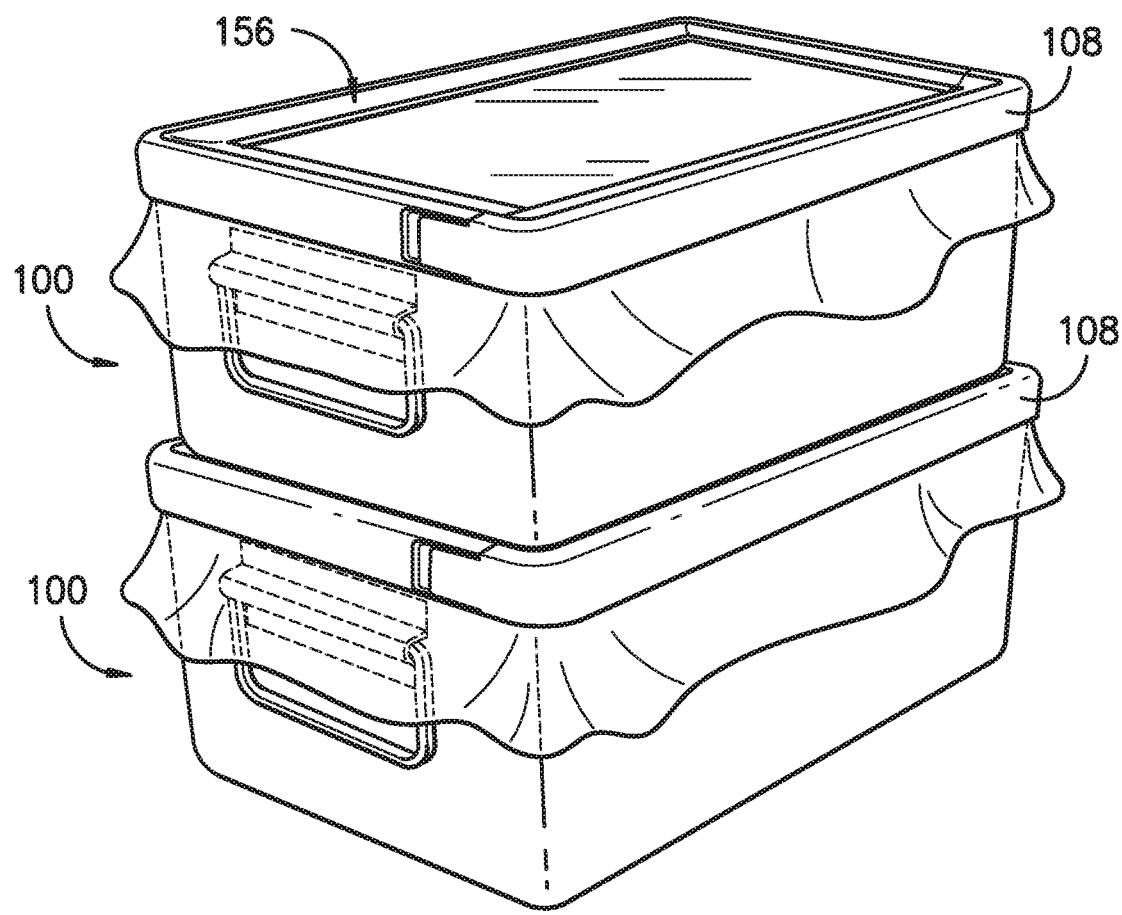
FIG. -7-

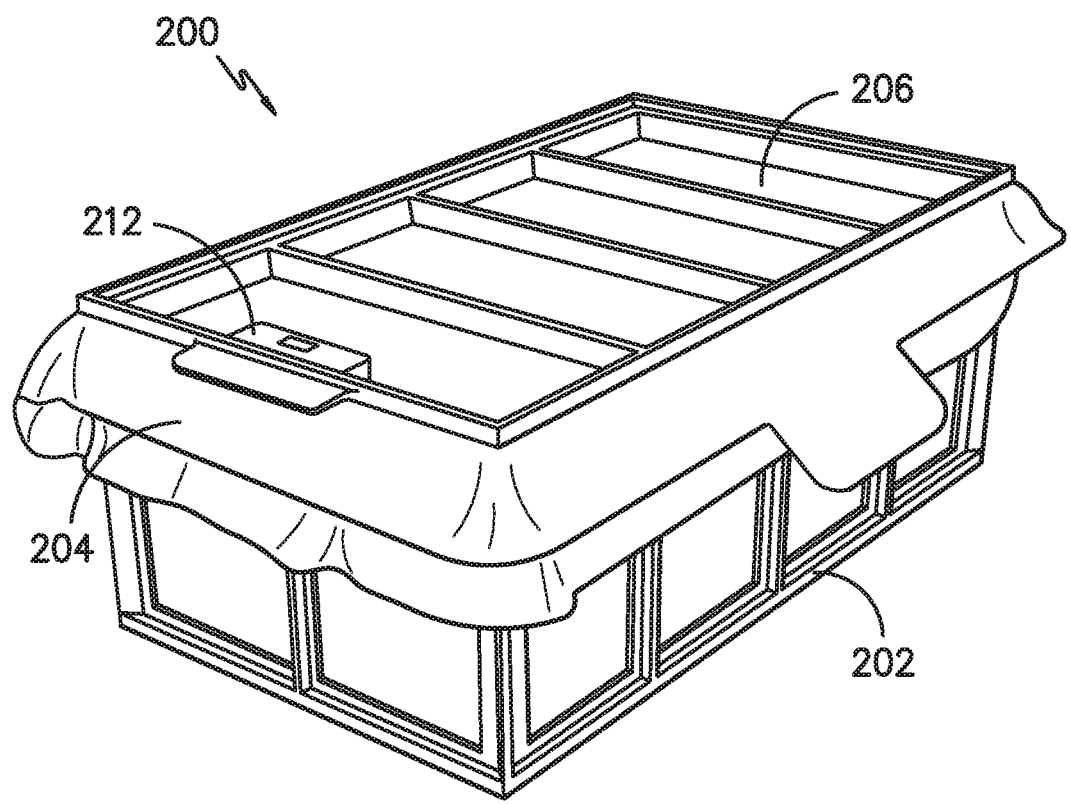
FIG. —8—

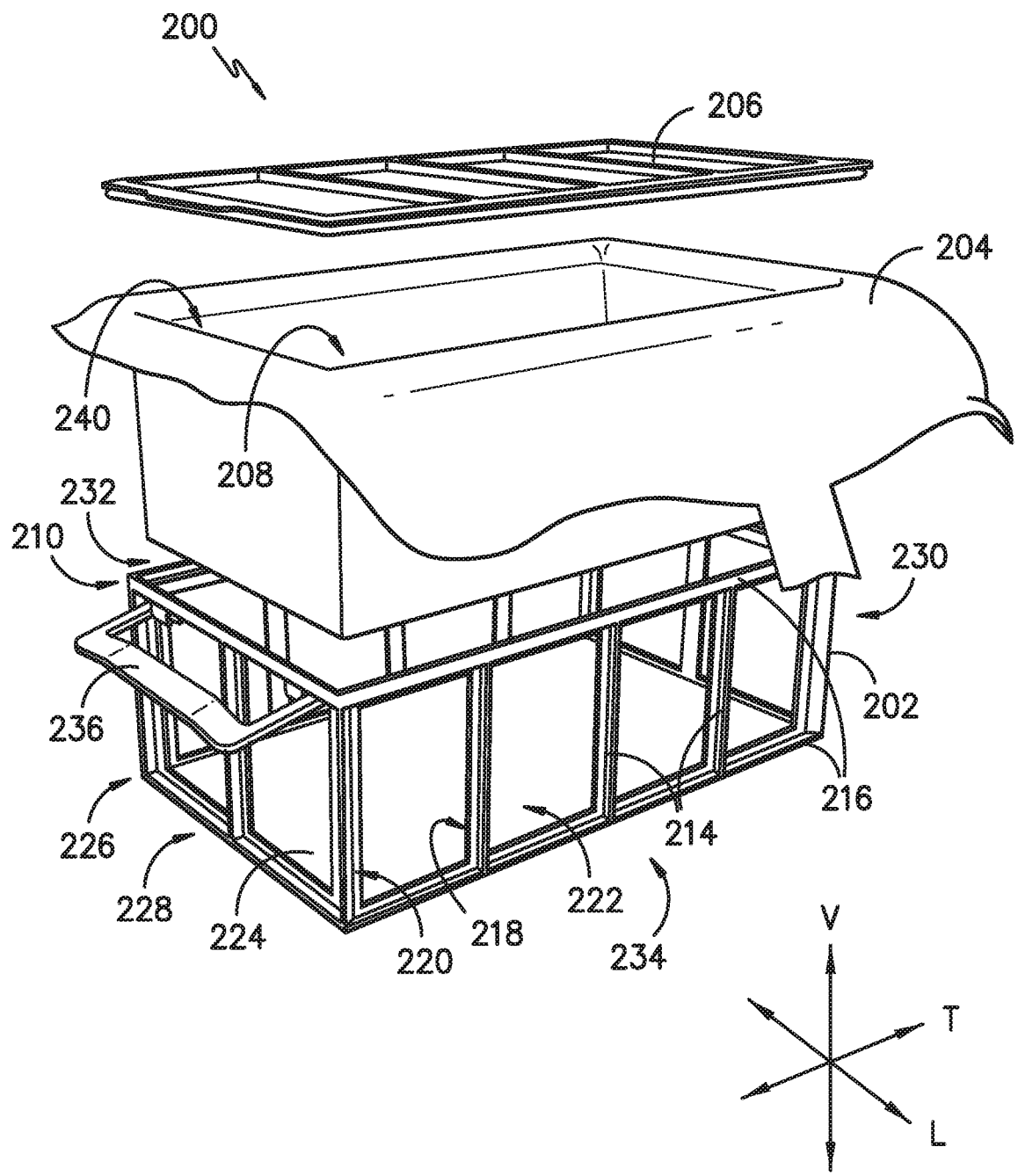
FIG. -9-

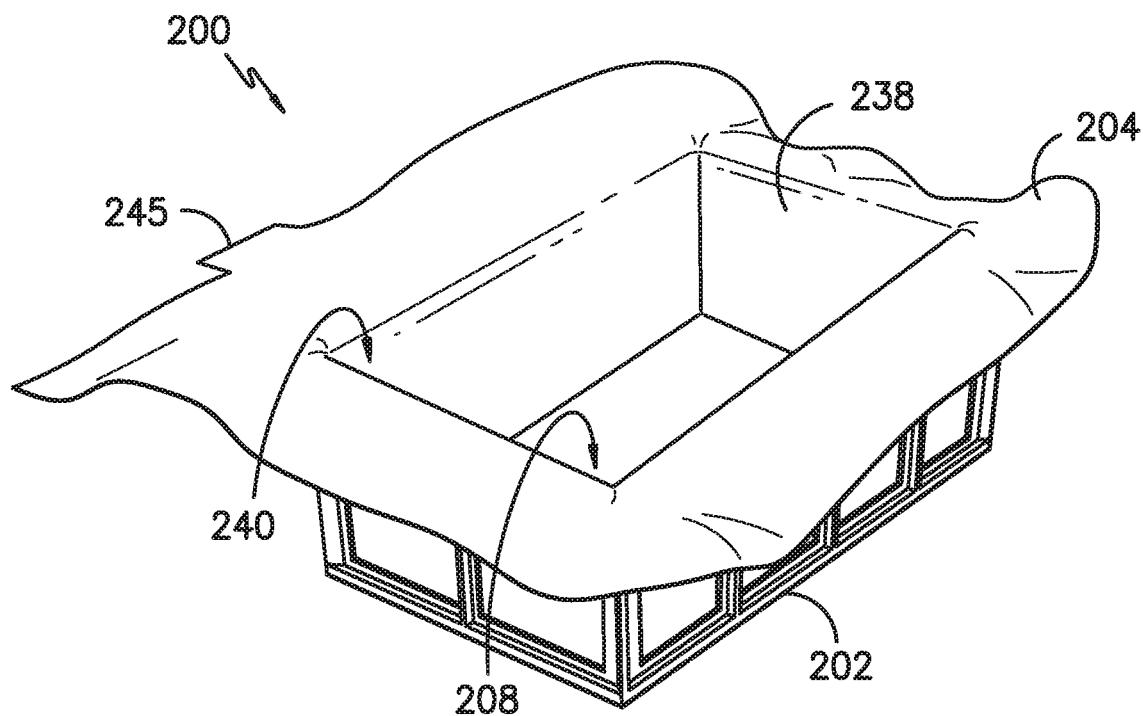
FIG. -10-
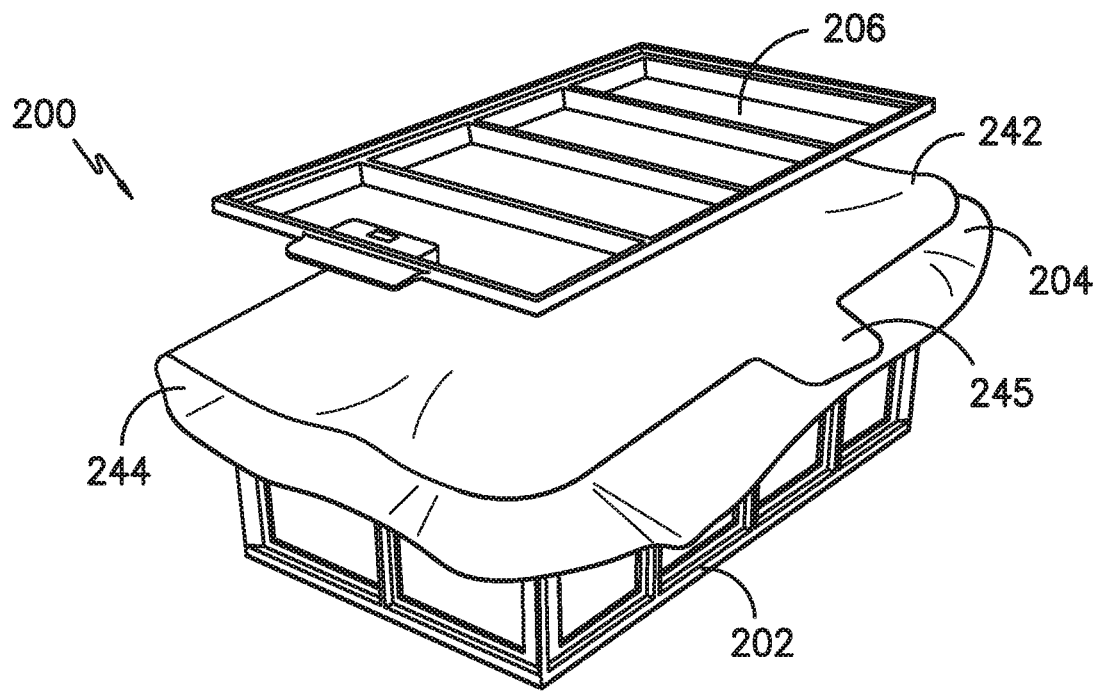
FIG. -11-

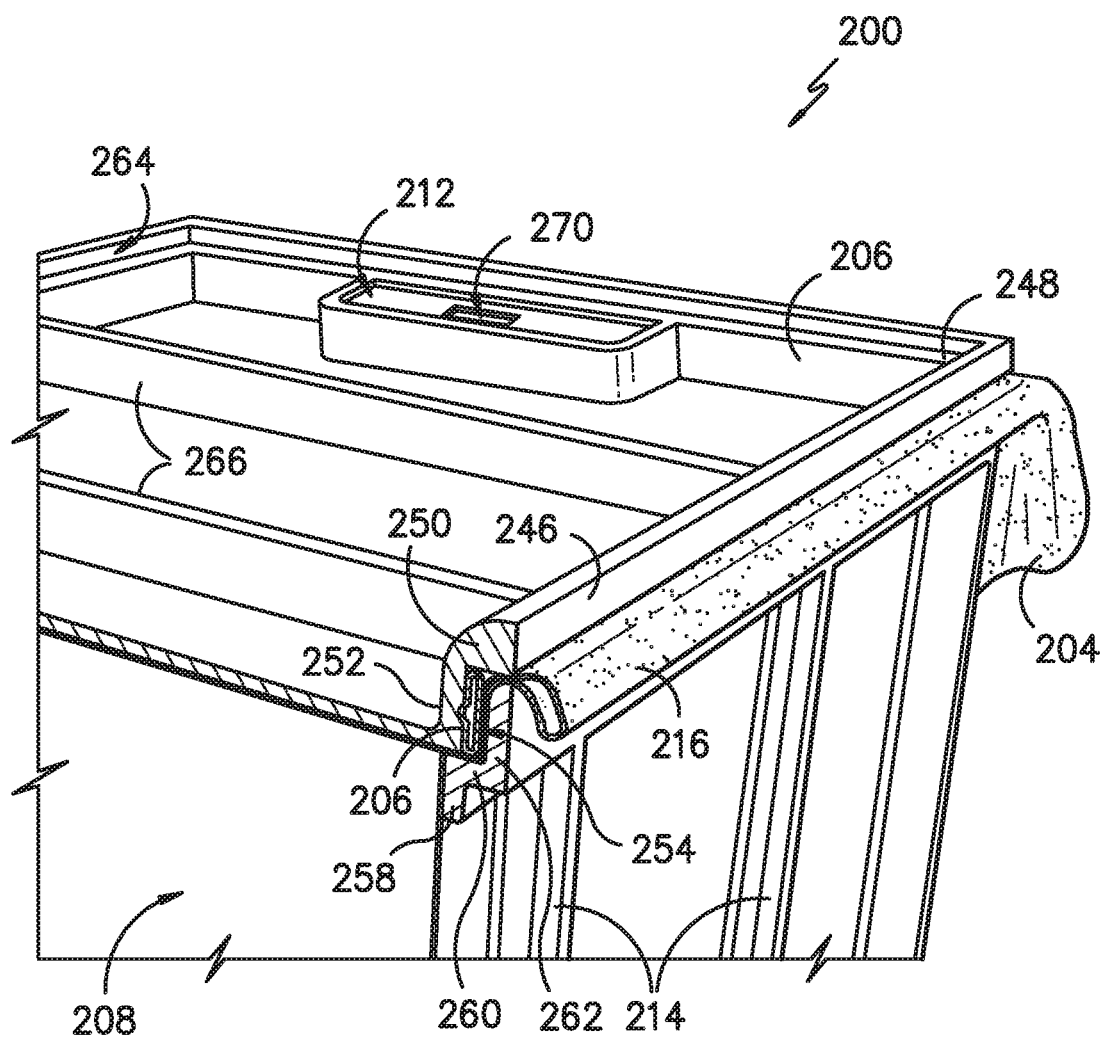
FIG. -12-

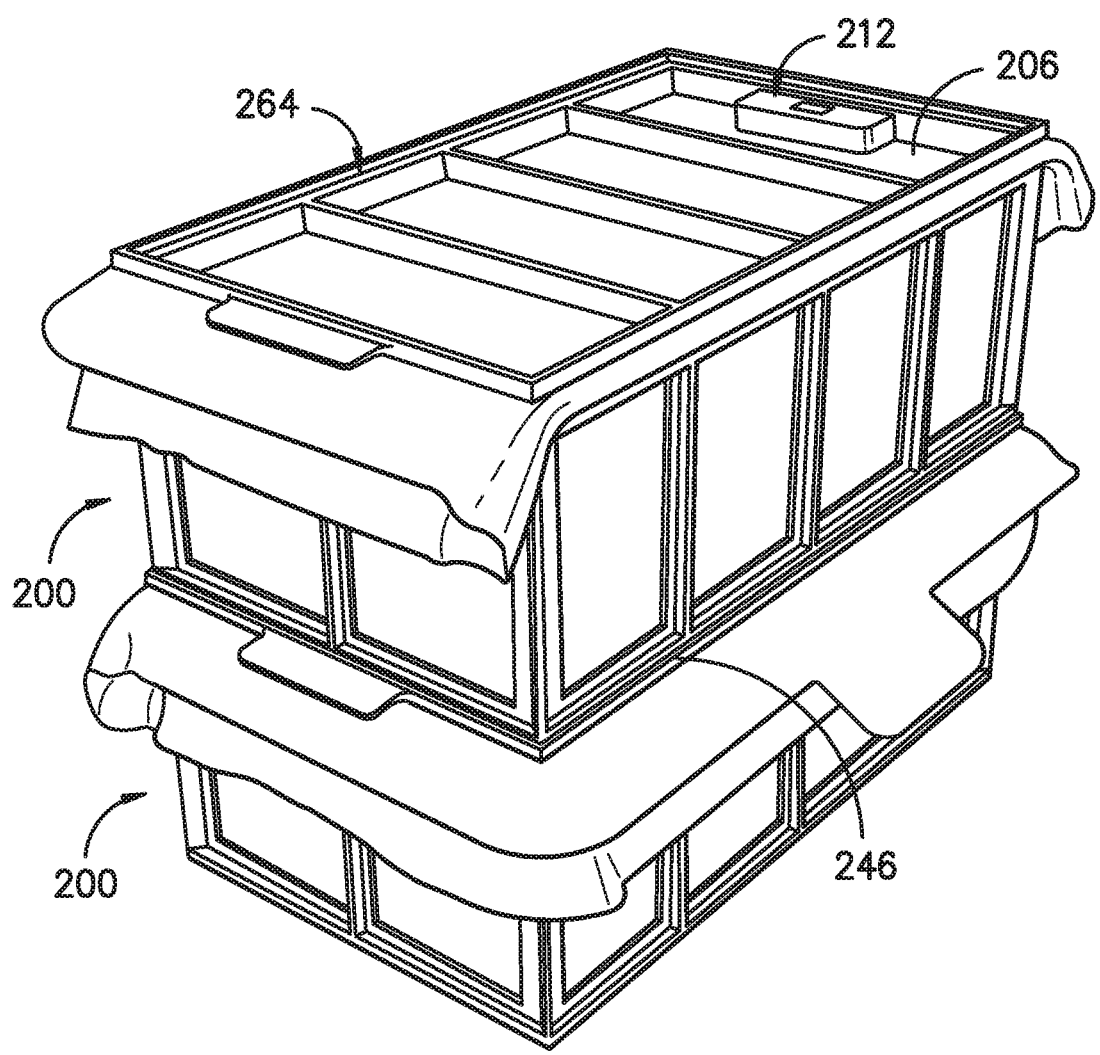
FIG. -13-

STERILIZATION PACKAGING SYSTEMS

CROSS-REFERENCE TO RELATED APPLICATIONS

This application is a national phase of and claims priority to PCT/US2016/58778, filed Oct. 26, 2016, which claims priority to U.S. Provisional Application Ser. No. 62/248,401, filed on Oct. 30, 2015, the contents of which applications are incorporated herein by reference thereto.

FIELD OF THE INVENTION

The subject matter of the present disclosure relates generally to sterilization packaging and sterilization packaging systems.

BACKGROUND

Personnel in the Central Service Room (CSR) or the Sterile Processing Department (SPD) of hospitals are commonly charged with the responsibility of packaging surgical supplies to ensure that the sterility of the packaged contents is maintained from sterilization to the point of reuse. Several activities are involved in the task of sterile supply delivery to the operating room and other units.

Much of the surgical instruments and supplies used in the operating room are reusable. These supplies typically include such things as clamps, scalpel blade handles, retractors, forceps, scissors, surgeon's towels, basins, and the like. All of these supplies must be collected after each procedure, decontaminated, placed in a sterilization packaging system, and sterilized before they can be used again in another procedure. The sterilization packaging systems used must be of the size and shape to accommodate the items to be sterilized and must be compatible with and withstand the physical conditions of the sterilization process.

Typical means of sterilizing instruments include, among others, autoclaving with steam, exposure to ethylene oxide gas, and exposure to hydrogen peroxide plasma, as is done with the STERRAD® Sterilization System from Advanced Sterilization Products, Irvine, Calif. After the package and its contents have been sterilized, the sterilization package typically is stored until it is needed for a surgical procedure.

Common sterilization packaging systems include sealable pouches, sterilization wraps, and rigid containers. Although each of these systems has some advantage compared to other systems, each of these typical packaging systems also has drawbacks. As an example, using a sterilization wrap to package items to be sterilized in a certain prescribed manner will permit the entry of sterilizing vapor/gas or other medium to sterilize the contents of the wrapped package while denying the ingress of contaminants such as bacteria and other infection causing materials or their vehicles after sterilization. As such, sterilization wraps generally provide a consistent barrier against the ingress of contaminants. However, during storage and transfer to the operating room, the wrapped package may be handled several different times; each time the wrapped package is handled, there is a potential that the sterile nature of the package contents can be compromised, e.g., by a tear, cut, or other breach of the wrapping material.

As another example, sterilization containers—such as, e.g., a metal box and a rigid top or lid that closes the metal box—also can permit the entry of sterilizing medium while denying the ingress of contaminants after sterilization. Unlike sterilization wraps, rigid sterilization containers usually avoid tears, cuts, and the like that can compromise the sterilized contents of the container. However, typical rigid sterilization containers are complex packaging systems, including several parts that must be precisely assembled to prevent compromising the contents of the container after sterilization. Further, some parts of the sterilization container assembly are prone to warping, denting, and breakage, as well as mismatching, loss, and/or other damage. Thus, even if the parts of the container can be assembled, damaged parts can prevent proper assembly of the sterilization container and thereby allow the ingress of contaminants after sterilization.

Consequently, there is a need for a sterilization packaging system that overcomes the shortcomings of known packaging systems. In particular, a sterilization packaging system that reduces the number of packaging components and the number of steps required to assemble the sterilization packaging system, while also minimizing the costs and amount of material required for the sterilization packaging system, would be beneficial. Additionally, a sterilization packaging system that provides a consistent barrier against the ingress of contaminants while avoiding post-sterilization breaches of the packaging system would be advantageous. Moreover, a sterilization packaging system that increases confidence that a sterilized package has not been breached also would be useful.

SUMMARY

The present invention provides sterilization packaging systems with features for sealing a volume against an ingress of contaminants. Such features include a sealing assembly, where the sealing assembly includes a sheet of sterilization material and a clamp for sealing the sheet of sterilization material against a container to seal the volume of the container from contaminants. The features further include a sterilization wrap and a lid for sealing a volume defined by the sterilization wrap and a frame. The present disclosure also provides a sealing assembly including a sheet of sterilization material and a clamp having open position and clamped positions. The clamp is configured to extend about a perimeter of a container, the sheet of sterilization material is disposed between the container and the clamp when the clamp is in the clamped position to seal a volume of the container, and the clamp is held in the clamped position by a latch. Additional aspects and advantages of the invention will be set forth in part in the following description, may be apparent from the description, or may be learned through practice of the invention.

In one aspect, the present subject matter is directed to a sterilization packaging system. The sterilization packaging system includes a container and a sealing assembly. The container defines a vertical direction and a volume for containing items to be sterilized, and the container has a perimeter defining an opening through which the items to be sterilized are placed in the container. The sealing assembly includes a sheet of sterilization material and a clamp. The clamp has an open position and a clamped position and extends about the perimeter of the container when in the clamped position. Further, the clamp is held in the clamped position by a latch. Accordingly, the sealing assembly is configured to seal the sheet of sterilization material against the container to seal the volume of the container from contaminants. In particular embodiments, the sealing assembly may be disposable. It should be understood that the sterilization packaging system may be further configured with any of the additional features as described herein.

In one embodiment, the container includes one or more vertical walls extending along the vertical direction and a horizontal wall extending perpendicular to the vertical direction. As such, the one or more vertical walls and the horizontal wall define the volume.

In another embodiment, the clamp includes a vertical portion extending along the vertical direction. The vertical portion is positioned adjacent one or more vertical walls of the container. The clamp further includes a horizontal portion extending perpendicular to the vertical portion. Accordingly, the horizontal portion of the clamp may define a window, and the sheet of sterilization material may be visible through the window.

In yet another embodiment, the clamp comprises a hinge portion opposite the latch. In some embodiments, the latch comprises a first arm defining a catch and a second arm defining a detent. In a further embodiment, one of the first arm or the second arm hinge about the hinge portion to place the clamp in the open position or the clamped position. In a still further embodiment, the first arm and the second arm may be portions of the clamp such that the clamp defines the latch.

In another embodiment, the sheet of sterilization material is disposed between clamp and container. The sheet of sterilization material may be a breathable film. In some embodiments, the breathable film may be transparent. In such embodiments, the items contained within the container may be visible through the breathable film.

In a further embodiment, the clamp of the sealing assembly comprises a protrusion defined by a vertical portion of the clamp. The protrusion extends inward toward the container. In additional embodiments, the container may define a groove such that the protrusion of the clamp protrudes into the groove when the clamp is positioned on the container. Accordingly, the protrusion may help seal the volume defined by the container.

In some embodiments, the clamp may have a generally L-shaped cross-section. Alternatively or additionally, the clamp may extend only partially across the opening defined by the perimeter of the container. However, in other embodiments, the clamp may extend fully across the opening. Moreover, in some embodiments, the clamp defines a depression. The depression may be configured such that a second sterilization packaging system may be stacked on top of the clamp.

In another aspect, the present subject matter is directed to a sealing assembly for a sterilization packaging system. The sealing assembly includes a sheet of sterilization material and a clamp. The clamp may have an open position and a clamped position. Further, the clamp may be configured to extend about a perimeter of a container for containing items to be sterilized, and the clamp may be held in the clamped position by a latch. The sheet of sterilization material may be disposed between the container and the clamp when the clamp is in the clamped position. As such, the sheet of sterilization material and the clamp seal a volume of the container against an ingress of contaminants. It should be understood that the sealing assembly may be further configured with any of the additional features as described herein.

In some embodiments, the sealing assembly is disposable. Moreover, in some embodiments the clamp includes a vertical portion extending along a vertical direction. The vertical portion may be positioned adjacent one or more vertical walls of the container. The clamp also may include a horizontal portion extending perpendicular to the vertical portion. In additional embodiments, the horizontal portion of the clamp defines a window.

In other embodiments, the clamp comprises a hinge portion opposite the latch. In some embodiments, the latch may include a first arm defining a catch and a second arm defining a detent. In additional embodiments, one of the first arm or the second arm hinge about the hinge portion to place the clamp in the open position or the clamped position. In still other embodiments, the first arm and the second arm are portions of the clamp such that the clamp defines the latch.

In another embodiment, the sheet of sterilization material is a breathable film. In appropriate embodiments, the breathable film may be transparent. As such, the items contained within the container may be visible through the breathable film.

In some embodiments, the clamp may comprise a protrusion defined by a vertical portion of the clamp. The protrusion may extend inward toward the container. In additional embodiments of the sealing assembly, the container defines a groove, and the protrusion of the clamp protrudes into the groove when the clamp is positioned on the container. Accordingly, the protrusion may help seal the volume of the container.

In another embodiment, the clamp has a generally L-shaped cross-section. Alternatively or additionally, the container may have a perimeter defining an opening through which the items to be sterilized are placed in the volume of the container. In some embodiments, the clamp extends only partially across the opening defined by the perimeter of the container. However, in other embodiments, the clamp may extend fully across the opening. In still other embodiments, the clamp defines a depression. The depression may be configured such that a sterilization packaging system may be stacked on top of the clamp.

In still another aspect, the present subject matter is directed to a sealing assembly for a sterilization packaging system. The sealing assembly includes a sheet of sterilization material and a clamp having an open position and a clamped position. The clamp is held in the clamped position by a latch, and the clamp defines a window. The clamp is configured to extend about a perimeter of a container for containing items to be sterilized, and the sheet of sterilization material is disposed between the container and the clamp when the clamp is in the clamped position to seal a volume of the container against an ingress of contaminants. Further, the sheet of sterilization material is visible through the window defined by the clamp when the clamp is in the clamped position. It should be appreciated that the sealing assembly may be further configured with any of the additional features as described herein.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 provides a perspective view of a sterilization container system as generally known in the art.

FIG. 2 provides a perspective view of a sterilization wrap system as generally known in the art.

FIG. 3 provides a perspective view of a sterilization packaging system having a clamp in a closed or clamped position according to an exemplary embodiment of the present subject matter.

FIG. 4 provides a perspective view of the sterilization packaging system of FIG. 3 with the clamp in an open position according to an exemplary embodiment of the present subject matter.

FIG. 5 provides a perspective, exploded view of the sterilization packaging system of FIG. 4.

FIG. 6 provides a partial cross-section view of the sterilization packaging system of FIG. 3.

FIG. 7 provides a perspective view of two stacked sterilization packaging systems according to an exemplary embodiment of the present subject matter.

FIG. 8 provides a perspective view of a sterilization packaging system according to an exemplary embodiment of the present subject matter.

FIG. 9 provides a perspective, exploded view of the sterilization packaging system of FIG. 8.

FIG. 10 provides a perspective view of a portion of the sterilization packaging system of FIG. 8.

FIG. 11 provides a perspective, partially exploded view of the sterilization packaging system of FIG. 8.

FIG. 12 provides a partial cross-section view of the sterilization packaging system of FIG. 8.

FIG. 13 provides a perspective view of two stacked sterilization packaging systems according to an exemplary embodiment of the present subject matter.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Described herein is a sterilization packaging system and components thereof suitable for use in a variety of procedures for containing, sterilizing, storing, and using sterilized items such as surgical supplies. While described in conjunction with its use in hospital and surgical room procedures, the present subject matter is intended for use wherever there is a need for sterilized materials. Consequently, the following description should not be considered a limitation as to the scope of use of the present subject matter.

FIG. 1 provides a perspective view of a sterilization container system as described above and as generally known in the art. In typical container systems, such as container system 10, one or more items to be sterilized are placed in a container 12, which generally is a rigid metal box. Container 12 may define one or more vents 14. A lid or top 16 is placed on container 12 to seal container 12 for sterilization. As shown, lid 16 may define one or more vents 18, and a gasket 20 may be positioned between lid 16 and container 12 to improve the seal between container 12 and lid 16. Further, typical sterilization container system 10 includes several filter assemblies 22, each filter assembly 22 having a filter 24, a retention plate 26, and multiple gaskets 28. As shown, the filter assemblies 22 usually are positioned within container system 10 adjacent vents 14, 18 defined by container 12 and lid 16. As will be readily understood, sterilization container system 10 generally is a complex assembly, comprising a multitude of parts that can be lost, damaged, or improperly assembled. Lost parts require replacement, which increases the cost of container system 10, and damaged or improperly assembled container systems 10 can lead to post-sterilization contamination of the items contained in container 12 by permitting the ingress of contaminants into the container system 10.

FIG. 2 provides a perspective view of a sterilization wrap system 50 as described above and as generally known in the art. To wrap an item for sterilization, such as one or more surgical implements or other items requiring sterilization, the item is placed on top of sterilization wrap 52 in contact with an inner surface of sterilization wrap 52 such that the four corners of sterilization wrap 52 can be folded over the item one at a time to fully wrap the item and form a wrapped package. Sterilization wrap 52 must be of a size large enough to fully wrap the items to be sterilized. Usually, each fold of the sterilization wrap 52 folds over most of the item or items to be sterilized, and each subsequent fold overlaps the previous fold, leaving the item or items to be sterilized completely encompassed within the folds of sterilization wrap 52. Further, a sealing mechanism 54, such as one or more of an adhesive, tape, mechanical fastener, or the like, may be applied to sterilization wrap 52 to hold the folds of wrap 52 in place. After wrapping, an outer surface 56 of sterilization wrap 52 forms the resulting exterior surfaces of the wrapped item or package. Alternatively, the items to be sterilized may be placed in a tray that is then wrapped with sterilization wrap 52 such that outer surface 56 of wrap 52 is the exterior surface of the wrapped package. Because sterilization wrap 52 forms the outer surface of sterilization wrap system 50, system 50 is prone to breaches such as, e.g., cuts, tears, or the like, which can lead to post-sterilization contamination of the wrapped items by permitting the ingress of contaminants into the wrapped package.

Referring now to FIGS. 3 and 4, perspective views are provided of a sterilization packaging system according to an exemplary embodiment of the present subject matter. In the depicted embodiment, sterilization packaging system 100 includes a container 102 for containing one or more items to be sterilized and a sealing assembly 104, which seals container 102 from the ingress of contaminants such as, e.g., bacteria and other infection causing materials or their vehicles. Sealing assembly 104 includes a sheet 106 of sterilization material and clamp 108. As shown in FIG. 3, clamp 108 has an open position for assembling sterilization packaging system 100 and for retrieving when needed the sterilized items within container 102, and as shown in FIG. 4, clamp 108 has a closed or clamped position for sealing container 102 against the ingress of contaminants. Once sealed, the sealed sterilization package can then be transferred to sterilizing equipment and exposed to sterilization conditions as generally known in the art. Such sterilization conditions can include, e.g., steam, ethylene oxide, or hydrogen peroxide plasma sterilization conditions. Sterilization conditions are the conditions present during a particular sterilization methodology utilized that substantially or completely destroys bacteria and other infectious organisms in an industrial or medical product.

Referring now to FIGS. 5 through 7, sterilization packaging system 100 will be described in greater detail. Container 102 defines a vertical direction V, a longitudinal direction L, and a transverse direction T, which are orthogonal to one another. Container 102 further defines a volume 110 for containing items to be sterilized. More particularly, container 102 includes one or more vertical walls 112 extending along the vertical direction V and one or more horizontal walls 114 extending perpendicular to the vertical direction. The one or more vertical and horizontal walls 112, 114 define volume 110.

In some embodiments, such as the depicted exemplary embodiment, container 102 may be generally rectangular in shape, having four vertical walls 112 and one horizontal wall 112 defining volume 110. In such embodiments, container 102 may define a first side 116 of sterilization packaging system 100 opposite a second side 118, e.g., first side 116 is spaced apart from second side 118 along transverse direction T, and a third side 120 opposite a fourth side 122, e.g., third side 120 is spaced apart from fourth side 122 along longitudinal direction L. Moreover, as shown, container 102 may include one or more handles 124, e.g., for ease in transporting sterilization packaging system 100. For example, one handle 124 may be attached or pivotally coupled to a vertical wall 112 at first side 116 of system 100 and another handle 124 may be attached or pivotally coupled to a vertical wall 112 at second side 118, i.e., handles 124 may be attached or coupled on opposite sides of container 102. Of course, container 102 also may have other shapes or configurations, e.g., container 102 may be generally round in shape, include walls at an angle to the vertical direction V, include any number of handles 124, or may omit handles 124.

Further, container 102 has a perimeter 126 defining an opening 128 through which the items to be sterilized are placed within volume 110 of container 102. Perimeter 126 generally is defined by an uppermost portion of vertical walls 112. As shown in FIG. 5, perimeter 116 is defined vertically opposite horizontal wall 114, i.e., in the illustrated embodiment, perimeter 126 is defined at the uppermost portion of vertical walls 112 and horizontal wall 114 is defined at the lowermost or bottommost portion of vertical walls 112. Referring particularly to FIG. 6, container 102 may define a groove 130 near perimeter 126. For example, groove 130 may be defined in vertical walls 112 and may extend about container 102 at a constant distance from perimeter 126.

As stated, sterilization packaging system 100 includes a sealing assembly 104 for sealing items within container 102, the sealing assembly including a sheet 106 of sterilization material and clamp 108. In exemplary embodiments of the present subject matter, sealing assembly 104 is disposable, i.e., both sheet 106 and clamp 108 may be disposed of after they are used to seal container 102, while container 102 may be reused. In other embodiments, sheet 106 and/or clamp 108 may be reusable.

As depicted in FIGS. 5 and 6, sterilization material sheet 106 is disposed between clamp 108 and container 102. More particularly, sheet 106 is positioned to extend across opening 128 of container 102 such that when clamp 108 is in the closed or clamped position on container 102, with the sheet 106 of sterilization material between clamp 108 and container 102, opening 128 is sealed closed to prevent the ingress of contaminants into volume 110. Further, as illustrated in FIGS. 5 and 6, an excess 132 of material may extend from beneath clamp 108, in a direction generally away from or outward from container 102, such that the excess material 132 defines a perimeter 134 of sterilization material sheet 106.

Sheet 106 can be made from a number of materials and, generally, may be made of a material from one of two main classes, reusables and disposables. Reusables are materials that, as the name suggests, can be reused, typically by washing or some other form of cleaning. Disposables, on the other hand, usually are one-use items that are discarded or recycled after their initial use. Generally, cloth, linen, or other woven materials fall into the reusable category while disposables normally include nonwoven materials made from either or both natural and synthetic fibers such as paper, fibrous polymeric nonwovens, and films, which are capable of passing sterilants and retarding transmission of bacteria and other contaminants.

Nonwoven sterilization materials present several advantages due to their barrier properties, economics, and consistent quality. The nonwoven materials can be made from a variety of processes including, but not limited to, air laying processes, wet laid processes, hydroentangling processes, spunbonding, meltblowing, staple fiber carding and bonding, and solution spinning. The fibers themselves can be made from a variety of both natural and synthetic materials including, but not limited to, cellulose, rayon, nylon, polyesters, polyolefins, and many other materials. The fibers may be relatively short, staple length fibers, typically less than three inches, or longer and substantially more continuous fibers such as are produced by spunbonding and meltblowing processes. Whatever materials are chosen, the resultant sterilization material 106 must be compatible with the particular sterilization technique being used and must also provide both strength and barrier properties to maintain the sterile nature of the contents of the sterilization package system 100 until use. In the illustrated exemplary embodiment, sheet 106 of sterilization material is a transparent breathable film, but in other embodiments, sheet 106 may be a translucent or opaque material, such as, e.g., a translucent breathable film, a SMS material (described below), or the like. For example, sheet 106 may be a sterilization wrap such as described in more detail below.

Referring still to FIGS. 5 and 6, in the illustrated embodiment, clamp 108 extends about perimeter 126 of container 102 when clamp 108 is in its closed or clamped position. Clamp 108 may be formed from a substantially rigid material, or in some embodiments, clamp 108 may be formed from a semi-rigid material such that clamp 108 can conform to perimeter 126 and/or the contours of container 102, which can aid in sealing container 102 when clamp 108 is closed or clamped onto container 102. Alternatively, clamp also may be formed from any other suitable material.

Clamp 108 is held in the closed or clamped position by a suitable securing mechanism, such as a latch 136. Referring particularly to FIG. 5, latch 136 comprises a first arm 138 defining a catch 140 and a second arm 142 defining a detent 144. In the depicted embodiment, first arm 138 and second arm 142 are portions of clamp 108, such that clamp 108 defines latch 136, i.e., latch 136 is integral with clamp 108. In other embodiments, latch 136 may be any suitable mechanism for holding or fastening clamp 108 in its closed or clamped position, e.g., latch 136 may be formed separately from clamp 108 and attached, coupled, or otherwise secured to clamp 108 to hold or fasten clamp 108 in the closed or clamped position.

As depicted in FIG. 5, clamp 108 includes a hinge portion 146 opposite latch 136. In the illustrated embodiment, second arm 142 of latch 136 pivots or hinges about hinge portion 146 to fasten detent 144 in catch 140 and thereby clamp or close clamp 108. Similarly, when detent 144 is unfastened from catch 140, second arm 142 pivots or hinges about hinge portion 146 to unclamp or open clamp 108. In other embodiments, first arm 138 defining catch 140 may pivot or hinge about hinge portion 146. In still other embodiments, clamp 108 may have other configurations for closing and opening to fasten and unfasten latch 136 or other securing mechanism for holding clamp 108 in place on container 102.

As further illustrated in FIGS. 5 and 6, clamp 108 includes a vertical portion 148 extending along the vertical direction V. Vertical portion 148 is positioned adjacent one or more vertical walls 112 of the container 102. Clamp 108 also includes a horizontal portion 150 that extends perpendicular to vertical portion 150. As depicted in FIG. 6, vertical portion 148 and horizontal portion 150 are arranged such that clamp 108 has a generally L-shaped cross-section. Of course, in other embodiments, clamp 108 may have other configurations, e.g., clamp 108 may include multiple vertical and horizontal portions 148, 150 or, additionally or alternatively, may include one or more portions that are at an angle with respected to the vertical direction V.

In the illustrated embodiment of clamp 108, for example, as shown in FIG. 4, horizontal portion 150 defines an opening or window 152. As shown, horizontal portion 150 extends about clamp 108 adjacent perimeter 126 of container 102, and more particularly, horizontal portion 150 extends inward from vertical portion 148 such that horizontal portion is adjacent opening 128 and volume 110 of container 102. However, horizontal portion 150 does not extend fully across opening 128, i.e., the clamp 108 extends only partially across opening 128 defined by the container 102, and a portion of sheet 106 of sterilization material is visible and/or accessible through window 152 defined by horizontal portion 150.

In other embodiments, horizontal portion 150 may extend fully across opening 128. That is, horizontal portion 150 may extend between a vertical portion 148 at first side 116 of sterilization packaging system 100, a vertical portion 148 at second side 118, a vertical portion 148 at third side 120, and a vertical portion 148 at fourth side 122. Accordingly, horizontal portion 150 may substantially cover opening 128, e.g., to protect sheet 106 of sterilization material that extends across opening 128 from punctures, cuts, tears, or like. In such embodiments, horizontal portion 150 may define one or more apertures for permitting the ingress of sterilization fluid and the egress of, e.g., water or other fluid (while sheet 106 of sterilization material prevent the ingress of contaminants as discussed).

Referring particularly to FIG. 6, exemplary clamp 108 also includes a protrusion 154 defined by vertical portion 148 of clamp 108. Protrusion 154 generally extends inward toward container 102. As illustrated in FIG. 6, when clamp 108 is positioned on container 102, protrusion 154 protrudes into groove 130 defined by container 102. As such, protrusion 154 may help seal container 102 and/or may help keep clamp 108 in place with respect to container 102.

As also illustrated in the exemplary embodiment of sterilization packaging system 100, clamp 108 defines a depression 156. Depression 156 generally is configured such that a second sterilization packaging system 100 may be stacked on top of clamp 108 of a first sterilization packaging system 100, as shown in FIG. 7. In the depicted embodiment, depression 156 substantially is a curved transition between vertical portion 148 and horizontal portion 150 of clamp 108. Other shapes, configurations, or the like of depression 156 may be used as well.

It will be readily understood that sterilization packaging system 100 requires fewer packaging components than prior art packaging systems using rigid containers. Accordingly, the number of steps required to assemble sterilization packaging system 100, as well the costs of and the material required for sterilization packaging system 100, is reduced compared to known systems. Additionally, sealing assembly 104, comprising sheet 106 of sterilization material and clamp 108, provides a consistent barrier against the ingress of contaminants while avoiding post-sterilization breaches of the packaging system. Thus, sterilization packaging system 100 can increase confidence in the continued sterility of items packaged therein after the package has been sterilized and stored. Of course, sterilization packaging system 100 also may have other benefits and advantages.

Referring now to FIG. 8, a perspective view is provided of a sterilization packaging system according to another exemplary embodiment of the present subject matter. In the depicted embodiment, sterilization packaging system 200 includes a frame 202, a sterilization wrap 204, and a top or lid 206. Generally, sterilization wrap 204 lines frame 202 to define a volume 208 for containing items to be sterilized. Lid 206 is positioned on a top portion 210 of frame 202, with sterilization wrap 204 disposed therebetween, to seal volume 208 from the ingress of contaminants such as, e.g., bacteria and other infection causing materials or their vehicles. Once sealed, the sealed sterilization package can then be transferred to sterilizing equipment and exposed to sterilization conditions as generally known in the art and as described elsewhere herein. A sterility gauge 212 also may be included to indicate whether the sterilized package has been breached.

Referring now to FIGS. 9 through 13, sterilization packaging system 200 will be described in greater detail. In the depicted embodiment, frame 202 defines a vertical direction V, a longitudinal direction L, and a transverse direction T, which are orthogonal to each other. Frame 202 includes a plurality of vertical members 214 extending along the vertical direction V and a plurality of horizontal members 216 extending perpendicular to the vertical direction V and vertical members 214. Each vertical member 214 and horizontal member 216 has an inner side 218 and an outer side 220. That is, inner side 218 is opposite outer side 220 such that each inner side 218 is oriented toward another inner side 218 and is positioned adjacent sterilization wrap 204 lining frame 202 to define volume 208. Together, vertical members 214 and horizontal members 216 define a plurality of windows 222, and sterilization wrap 204 is visible and/or accessible through windows 222. As shown in FIG. 9, frame 202 also includes a horizontal bottom panel 224 extending perpendicular to the vertical direction V and vertical members 214 and between horizontal members 216 at a bottom portion 226 of frame 202. Bottom portion 226 is generally vertically opposite top portion 210 of frame 202.

In some embodiments, frame 202 is constructed from a rigid material. In alternative embodiments, frame 202 is constructed from semi-rigid or other materials. In any event, frame 202—having vertical members 214, horizontal members 216, and bottom panel 224—provides structure to and/or strengthens sterilization wrap 204 to help prevent breaches of sterilization wrap 204 due to, e.g., cuts, tears, or the like.

In the depicted exemplary embodiment, frame 202 is generally rectangular in shape, having four vertical sides defined by vertical and horizontal members 214, 216 and a horizontal bottom panel 224. In such embodiments, frame 202 may define a first side 228 of sterilization packaging system 200 that is opposite a second side 230, e.g., first side 228 is spaced apart from second side 230 along transverse direction T, and a third side 232 opposite a fourth side 234, e.g., third side 232 is spaced apart from fourth side 234 along longitudinal direction L. Moreover, as shown in FIG. 9, frame 202 may include one or more handles 236, e.g., for ease in transporting sterilization packaging system 200. For example, one handle 236 may be attached or pivotally coupled to a horizontal member 216 at first side 228 of system 200 and another handle 236 may be attached or pivotally coupled to a horizontal member 216 at second side 230, i.e., handles 236 may be attached or coupled on opposite sides of frame 202. Of course, frame 202 may have other shapes or configurations as well, e.g., frame 202 may be generally round in shape, include members at an angle to the vertical direction V, include any number of handles 236, or may omit handles 236.

As illustrated most clearly in FIGS. 9 and 10, sterilization wrap 204 may be shaped to closely match the shape enclosed by frame 202 and thereby line frame 202 to define volume 208. In other embodiments, sterilization wrap 204 may be positioned within frame 202 to generally match the shape enclosed by frame 202. In either case, a first portion 238 of sterilization wrap 204 is positioned adjacent inner side 218 of vertical and horizontal members 214, 216 to define volume 208 and an opening 240 to access volume 208. As shown in FIG. 11, sterilization wrap 204 may be folded over to define a second portion 242 of sterilization wrap 204. Second portion 242 is thereby positioned across opening 240 to cover opening 240. Further, when sterilization wrap 204 is folded to define second portion 242, a fold 244 is defined between second portion 242 and first portion 238 of sterilization wrap 204. Moreover, in some embodiments, sterilization wrap 204 may include a tab 245 to assist in positioning sterilization wrap 204, e.g., for use as a grip when folding over sterilization wrap 204 to position second portion 242 across opening 240.

Like sheet 106 of sterilization material described above, sterilization wrap 204 can be made from a number of materials and, generally, may be a material from one of the two main classes, reusables and disposables, previously described. It has been found that polyolefin-based fibers and their resultant nonwovens are particularly well-suited for the production of sterilization wrap 204. Polypropylene spunbonded nonwovens such as are produced by Halyard Health, Inc. of Alpharetta, Ga., can be used to impart strength characteristics to sterilization wrap 204. In some embodiments, sterilization wrap 204 may be made from laminates such as a laminate of spunbonded and meltblown or spunbonded, meltblown, spunbonded to impart both strength and barrier properties to sterilization wrap 204.

A spunbonded-meltblown-spunbonded material is made from three separate layers that are laminated to one another. The method of making these layers is known and described in U.S. Pat. No. 4,041,203 to Brock, et al., which is incorporated herein in its entirety by reference. The material of Brock, et al. is a three layer laminate of spunbonded-meltblown-spunbonded layers that is also commonly referred to by the acronym "SMS." The two outer layers of SMS are a spunbonded material made from extruded polyolefin fibers, or filaments, laid down in a random pattern and then bonded to one another. The inner layer is a meltblown layer also made from extruded polyolefin fibers generally of a smaller diameter than the fibers in the spunbonded layers. As a result, the meltblown layer provides increased barrier properties due to its fine fiber structure, which permits the sterilizing agent to pass through the fabric while preventing passage of bacteria and other contaminants. Conversely, the two outer spunbonded layers provide a greater portion of the strength factor in the overall laminate. The laminate may be prepared using an intermittent bond pattern that is preferably employed with the pattern being substantially regularly repeating over the surface of the laminate. The pattern is selected such that the bonds may occupy about 5% to about 50% of the surface area of the laminate. Desirably, the bonds may occupy about 10% to about 30% of the surface area of the laminate. In an exemplary embodiment, sterilization wrap 204 is made from a SMS material, but sterilization wrap 204 also may be made from other suitable materials.

As illustrated, sterilization packaging system 200 includes lid 206 for sealing volume 208 against an ingress of contaminants. Referring particularly in FIG. 12, lid 206 is positioned at top portion 210 of frame 202 in contact with second portion 242 of sterilization wrap 204 to seal volume 208. More specifically, lid 206 generally has a shape complementary to a shape defined by top portion 210 of frame 202 such that when lid 206 is positioned at top portion 210, lid 206 seals volume 208 by preventing access to opening 240. In exemplary embodiments of the present subject matter, sterilization wrap 204 is disposable, i.e., sterilization wrap 204 may be disposed of after it is used within sterilization packaging system 200, while frame 202 and lid 206 may be reused. In other embodiments, as described above, sterilization wrap 204 also may be reusable.

Continuing with FIG. 12, lid 206 comprises a lip 246 defined along a perimeter 248 of lid 206. Lid 206 further includes a flange comprising a horizontal flange portion 250 adjacent lip 246 and a vertical flange portion 252 adjacent horizontal flange portion 250. Horizontal and vertical flange portions 250, 252 define a recess 254. An inflatable gasket 256 is positioned in recess 254. As also illustrated, horizontal member 216 of frame 202 defines a corresponding lip 258 and a flange comprising horizontal flange portion 260 and vertical flange portion 262. In the depicted embodiment, horizontal flange portion 250 of the lid flange rests on vertical flange portion 262 of the frame flange, and vertical flange portion 252 of the lid flange rests on horizontal flange portion 260 of the frame flange. Thus, gasket 256 inflates within recess 254 between flange portions 250, 252 of lid 206 and flange portions 260, 262 of frame 202. Once inflated, gasket 256 compresses sterilization wrap 204 between lid 206 and frame 202 to help seal volume 208 from contaminants. It will be readily understood that, in other embodiments, a suitable noninflatable gasket 256 may be used to help seal volume 208 from contaminants and/or other configurations of lid lip 246 and flange 250, 252 and frame lip 258 and flange 260, 262 may be used.

As further shown in the illustrated embodiment, lip 246 and horizontal flange portion 250 of lid 206 defines a depression 264 along perimeter 248 of lid 206. Depression 264 generally is configured such that a second sterilization packaging system 200 may be stacked on top of lid 206 of a first sterilization packaging system 200, as shown in FIG. 13. In the depicted embodiment, depression 264 substantially is a linear transition between lip 246 and horizontal flange portion 250. Lid 206 also includes a plurality of ribs 266. In the illustrated exemplary embodiment, ribs 266 extend horizontally between third side 232 and fourth side 234 of sterilization packaging system 200, i.e., generally between a portion of depression 264 defined along third side 232 and a portion of depression 264 defined along fourth side 234. Ribs 266 may provide rigidity to lid 206 and/or may support a sterilization packaging system 200 stacked on top of lid 206. Of course, in alternative embodiments, depression 264 and ribs 266 may have other shapes, configurations, or the like.

Moreover, lid 206 may include one or more gripping portions 268, e.g., for ease in positioning lid 206 to seal volume 208. For example, one gripping portion 268 may be attached to or defined by lid 206 at first side 228 of system 200 and another gripping portion 268 may be attached to or defined by lid 206 at second side 230, i.e., gripping portions 268 may be attached to or defined on opposite sides of lid 206. Of course, lid 206 may include any number of gripping portions 268, which may be attached to or defined at any appropriate location of lid 206, or in some embodiments, gripping portions 268 may be omitted.

Sterilization packaging system 200 further includes a sterility gauge 212 for signaling whether volume 208 is sealed against contaminants or has been breached. As such, in an exemplary embodiment, sterility gauge 212 comprises a binary visual signal, i.e., a signal having two outputs. For example, sterility gauge 212 may provide, as one of the two outputs of the binary signal, a green indicia in a viewport 270 of gauge 212 if sterilization packaging system 200 remains sterile, i.e., if the seal remains intact and volume 208 has not be breached post-sterilization. Sterility gauge 212 may provide, as the other of the two outputs of the binary signal, a red indicia in viewport 270 if system 200 is no longer sterile, i.e., if volume 208 has been breached since the sealed package was sterilized such that the package should not be used. Sterility gauge 212 also may be configured to provide the red indicia before the sealed package is sterilized and to provide the green indicia upon exposure to sterilization conditions; a subsequent breach of the package causes the signal to revert to the red indicia. As shown in, e.g., FIGS. 11 and 12, sterility gauge 212 may be positioned on lid 206; for example, sterility gauge 212 may be positioned on lid 206 adjacent first side 228 or second side 230 of sterilization packaging system 200. Other configurations and outputs of sterility gauge 212 may be used as well.

It will be readily understood that sterilization packaging system 200 helps prevent cuts, tears, and the like that are common breaches in known sterilization wrap packages. Accordingly, sterilization packaging system 200 utilizes the advantages of sterilization wraps, e.g., providing a consistent barrier against the ingress of contaminants, while substantially avoiding disadvantages such as, e.g., tears, cuts, or other breaches, particularly in areas such as corners and edges that are prone to such breaches. Moreover, features such as, e.g., sterility gauge 212 can increase confidence that a sterilized package has not been breached. Sterilization packaging system 200 also may have other benefits and advantages.

Although described separately, the disclosure with respect to sterilization packaging system 100 also may be applicable to sterilization packaging system 200 and vice versa. That is, some features described with respect to one system may also be used with the other system, e.g., in place of or in addition to features of the other system. As one example, sterility gauge 212 also may be included with sterilization packaging system 100 for indicating whether a package sealed according to system 100 has been breached, i.e., for indicating whether the seal of system 100 remains intact.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A sterilization packaging system, comprising:
   a container defining a vertical direction and a volume for containing items to be sterilized, the container having a perimeter defining an opening through which the items to be sterilized are placed in the container; and
   a sealing assembly, the sealing assembly including
      a sheet of sterilization material, and
      a clamp for sealing the sheet of sterilization material against the container to seal the volume of the container from contaminants, the clamp having an open position and a clamped position, the clamp extending about the perimeter of the container when the clamp is in the clamped position, the clamp comprising a first arm defining a catch and a second arm defining a detent, the catch and the detent forming a latch integrally formed with the clamp, the clamp further comprising
         a vertical portion extending along the vertical direction, the vertical portion positioned adjacent one or more vertical walls of the container, and
         a horizontal portion extending perpendicular to the vertical portion, the horizontal portion defining a window, the horizontal portion extending inward with respect to the perimeter of the container such that the horizontal portion is positioned over the opening,
   wherein the sheet of sterilization material extends between the clamp and the container such that the clamp contacts the sheet of sterilization material rather than the container, and
   wherein the clamp is held in the clamped position by the latch.

2. The sterilization packaging system of claim 1, wherein the sealing assembly is disposable.

3. The sterilization packaging system of claim 1, wherein the clamp comprises a hinge portion opposite the latch.

4. The sterilization packaging system of claim 3, wherein one of the first arm or the second arm hinges about the hinge portion to place the clamp in the open position or the clamped position.

5. The sterilization packaging system of claim 1, wherein the sheet of sterilization material is a breathable film.

6. The sterilization packaging system of claim 5, wherein the breathable film is transparent.

7. The sterilization packaging system of claim 1, wherein the clamp comprises a protrusion defined by a vertical portion of the clamp and the container defines a groove, and wherein the protrusion of the clamp protrudes into the groove when the clamp is positioned on the container.

8. The sterilization packaging system of claim 1, wherein the clamp defines a depression, the depression configured such that a second sterilization packaging system may be stacked on top of the clamp and received in the depression.

9. The sterilization packaging system of claim 8, wherein the clamp curves from the vertical portion toward the horizontal portion to define the depression such that the depression is a curved transition between the vertical portion and the horizontal portion of the clamp.

10. The sterilization packaging system of claim 1, wherein an excess of material of the sheet of sterilization material extends from beneath the clamp in a direction outward from the container.

11. The sterilization packaging system of claim 1, wherein the sheet of sterilization material is configured to pass sterilants to the volume for containing the items and to retard transmission of contaminants to the volume.

12. The sterilization packaging system of claim 1, wherein the vertical portion intersects with the horizontal portion such that the clamp has an L-shaped cross-section.

13. The sterilization packaging system of claim 1, wherein the vertical portion projects vertically above the horizontal portion, wherein the horizontal portion is planar, and wherein the clamp curves from the vertical portion to the horizontal portion.

14. A sealing assembly for a sterilization packaging system, the sealing assembly comprising:
a sheet of sterilization material; and
a clamp, the clamp having an open position and a clamped position, the clamp further having an L-shaped cross-section formed by a vertical portion including a planar surface and a horizontal portion including a planar surface,
wherein the clamp is configured to extend about a perimeter of a container for containing items to be sterilized,
wherein the sheet of sterilization material is disposed between the container and the clamp such that the clamp contacts the sheet of sterilization material rather than the container when the clamp is in the clamped position to seal a volume of the container against an ingress of contaminants, and
wherein the clamp is held in the clamped position by a latch, the latch comprising a catch defined by a first arm of the clamp and a detent defined by a second arm of the clamp such that the latch is integral with the clamp, the detent configured to fasten in the catch to hold the clamp in the clamped position.

15. The sealing assembly of claim 14, wherein the sealing assembly is disposable.

16. The sealing assembly of claim 14, wherein the vertical portion extends along a vertical direction, the vertical portion positionable adjacent one or more vertical walls of the container, and
the horizontal portion extends perpendicular to the vertical portion, the horizontal portion defining a window.

17. The sealing assembly of claim 14, wherein the clamp comprises a hinge portion opposite the latch, and wherein one of the first arm or the second arm hinge about the hinge portion to place the clamp in the open position or the clamped position.

18. The sealing assembly of claim 14, wherein the sterilization material is a spunbonded-meltblown-spunbonded material.

19. A sealing assembly for a sterilization packaging system, the sterilization packaging system including a container for containing items to be sterilized, the sealing assembly comprising:
a sheet of sterilization material configured to pass sterilants to a volume defined by the container for containing the items and to retard transmission of contaminants to the volume, and
a clamp having an open position and a clamped position, the clamp including
a vertical portion extending along a vertical direction, the vertical portion positionable adjacent one or more vertical walls of the container,
a horizontal portion extending perpendicular to the vertical portion, the horizontal portion defining a window,
a first arm defining a catch, and
a second arm defining a detent, the catch and the detent forming a latch integrally formed with the clamp for holding the clamp in the clamped position,
wherein the clamp is configured to extend about a perimeter of the container, the perimeter defining an opening through which the items to be sterilized are placed in the container, the horizontal portion of the clamp extending horizontally from the perimeter over the opening,
wherein the sheet of sterilization material is disposed under the vertical and horizontal portions of the clamp between the container and the clamp such that the clamp contacts the sheet of sterilization material rather than the container when the clamp is in the clamped position to seal the volume of the container against an ingress of contaminants, and
wherein the sheet of sterilization material is visible through the window defined by the horizontal portion of the clamp when the clamp is in the clamped position.

20. The sealing assembly of claim 19, wherein the vertical portion of the clamp defines a protrusion and the container defines a groove extending about the container, and wherein when the clamp is positioned on the container, the protrusion of the clamp protrudes into the groove with the sheet of sterilization material disposed between the protrusion and the groove.

* * * * *